United States Patent
De Sausmarez Lintell (10) Patent No.: US 8,747,365 B2
(45) Date of Patent: Jun. 10, 2014

(54) NEEDLE CANNULA CONTAINING MEDICAMENT

(75) Inventor: Daniel Thomas De Sausmarez Lintell, Warwickshire (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 0 days.

(21) Appl. No.: 13/882,082

(22) PCT Filed: Oct. 31, 2011

(86) PCT No.: PCT/EP2011/069105
§ 371 (c)(1),
(2), (4) Date: Apr. 26, 2013

(87) PCT Pub. No.: WO2012/059456
PCT Pub. Date: May 10, 2012

(65) Prior Publication Data
US 2013/0218088 A1 Aug. 22, 2013

(30) Foreign Application Priority Data
Nov. 3, 2010 (EP) .................................. 10189791

(51) Int. Cl.
*A61M 5/00* (2006.01)
*A61M 5/19* (2006.01)
*A61M 5/178* (2006.01)

(52) U.S. Cl.
CPC .......... *A61M 5/19* (2013.01); *A61M 2005/1787* (2013.01)
USPC .......................................................... 604/191

(58) Field of Classification Search
CPC .......... A61M 2005/1787; A61M 5/19; A61M 5/2425

USPC .......................................................... 604/191
See application file for complete search history.

(56) References Cited

U.S. PATENT DOCUMENTS 5,810,884 A * 9/1998 Kim .............................. 606/213
6,346,095 B1 2/2002 Gross et al.

FOREIGN PATENT DOCUMENTS

EP 0401822 A2 12/1990

OTHER PUBLICATIONS

Form PCT/IB/326, Notification Concerning Transmittal of International Preliminary Report on Patentability, May 16, 2013.

* cited by examiner

*Primary Examiner* — Laura Bouchelle
*Assistant Examiner* — Melissa A Snyder
(74) *Attorney, Agent, or Firm* — McDonnell Boehnen Hulbert & Berghoff LLP (57) ABSTRACT

A method and system of delivering a first medicament to a first injection depth and a second medicament to a second injection depth using a single dispense interface. An example medicated module is attachable to a drug delivery device, where the drug delivery device includes a drug reservoir holding a first medicament. The medicated module includes a needle cannula having a sidewall, at least one micro-hole in the sidewall of the needle cannula, and a flexible membrane sealably fixed to an inner surface of the needle cannula. The flexible membrane holds a second medicament between the flexible membrane and a portion of the sidewall having the at least one micro-hole. The first and second medicaments can be delivered to two, axially separate injection depths.

11 Claims, 5 Drawing Sheets

NEEDLE CANNULA CONTAINING MEDICAMENT

CROSS REFERENCE TO RELATED APPLICATIONS

The present application is a U.S. National Phase Application pursuant to 35 U.S.C. §371 of International Application No. PCT/EP2011/069105 filed Oct. 31, 2011, which claims priority to European Patent Application No. 10189791.6 filed Nov. 3, 2010. The entire disclosure contents of these applications are herewith incorporated by reference into the present application.

FIELD OF INVENTION

This present patent application relates to medical devices and methods of delivering at least two drug agents to different depths within a single injection site using devices having only a single dose setting mechanism and a single dispense interface. A single delivery procedure initiated by the user causes a non-user settable dose of a second drug agent and a variable set dose of a first drug agent to be delivered to the patient. The first drug agent may be available in a reservoir, container or package disposed in a primary drug delivery device. The second drug agent may be stored in a medicated module (and specifically in a medicated needle cannula) that is attachable to the primary drug delivery device. The drug agents may be independent (single drug compound) or pre-mixed (co-formulated multiple drug compounds) drug agents. Specifically, this application concerns a medicated needle cannula containing a medicament. The needle cannula is configured in such that, when it is attached to a primary delivery device containing another medicament, the medicated needle cannula is operable to deliver medicament to two different, axially separate depths within a single injection site.

BACKGROUND

Certain disease states require treatment using one or more different medicaments. Some drug compounds need to be delivered in a specific relationship with each other in order to deliver the optimum therapeutic dose. The presently proposed devices and methods are of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more active agents may require a titration period to gradually introduce a patient up to a "maintenance" dose. A further example would be if one active agent requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more that one drug delivery system or make the necessary accurate calculation of the required dose combination. This is especially true for users with dexterity or computational difficulties. In some circumstances it is also necessary to perform a priming procedure of the device and/or needle cannula before dispensing the medicaments.

For some drug combinations where a multi-drug compound therapy is required, it may be desirable to deliver medicament to two effectively separate depths within a single injection site. For instance, it may be desirable to deliver medicament to two effectively separate injection depths so that the two medicaments have minimal opportunity to mix in vivo. Currently, delivering medicament to two different injection site depths would necessitate two injections and potentially using two discrete injection devices.

Accordingly, there exists a need to provide devices and methods for the delivery of two or more medicaments to two effectively separate injection depths in a single injection or delivery step that is simple for the user to perform.

The presently proposed devices and methods overcome the above-mentioned problems by providing separate storage for two or more active drug agents that are then delivered to effectively separate injection depths in the patient during a single delivery procedure. Setting a dose of one medicament automatically fixes or determines the dose of the second medicament (i.e., non-user settable). The proposed devices and methods also give the opportunity for varying the quantity of one or both medicaments. For example, one fluid quantity can be varied by changing the properties of the injection device (e.g., dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime. The proposed medicated module includes a medicated needle cannula that holds a non-user-settable dose of medicament.

These and other advantages will become evident from the following more detailed description of the invention.

SUMMARY

The presently proposed devices and methods allow for complex combinations of multiple drug compounds within a single drug delivery system. Further, the presently proposed devices and methods allow the user to set and dispense at least two drug agents to effectively different injection depths through one single dose setting mechanism and a single dispense interface. This single dose setter controls the dose setting mechanism of the device such that a predefined combination of the individual drug compounds is delivered when a single dose of one of the medicaments is set and dispensed through the single dispense interface.

By defining the therapeutic relationship between the individual drug compounds, the proposed delivery device and delivery methods help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or gases or powders that are capable of flowing and that change shape at a steady rate when acted upon by a force tending to change its shape. Alternatively, in some embodiments, one or both of the medicaments may be a solid that is carried, solubilized or otherwise dispensed with another fluid medicament.

Applicant's proposed concept is of particular benefit to users with dexterity or computational difficulties as the single input and associated predefined therapeutic profile removes the need for them to calculate their prescribed dose every time they use the device and the single input allows considerably easier setting and dispensing of the combined compounds.

In a preferred embodiment a master drug compound, such as insulin, contained within a multiple dose, user selectable drug delivery device could be used with a single use, user replaceable, medicated module that contains a single dose of a secondary medicament and the single dispense interface. When connected to the primary drug delivery device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our proposed method and system.

For the purposes of our proposed method and system the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg (B32) human insulin; Lys(B3), Glu(B29) human insulin; Lys (B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

According to an embodiment, a medicated module is attachable to a drug delivery device, and the drug delivery device has a drug reservoir holding a first medicament. The medicated module comprises a needle cannula having a sidewall, at least one micro-hole in the sidewall of the needle cannula, and a flexible membrane sealably fixed to an inner surface of the needle cannula. The flexible membrane holds a second medicament between the flexible membrane and a portion of the sidewall having the at least one micro-hole.

According to another embodiment, a medicated module is attachable to a drug delivery device, and the drug delivery device has a drug reservoir holding a first medicament. The medicated module includes a needle cannula having a sidewall and at least one micro-hole in the sidewall of the needle cannula. A second medicament is located within the at least one micro-hole.

According to yet another embodiment, a method of delivering a primary medicament to a first injection depth and a second medicament to a second injection depth using a single dispense interface is provided. The method includes the step of attaching a medicated module to a drug delivery device, the drug delivery device having a primary drug reservoir holding the primary medicament. The medicated module comprises a needle cannula having a sidewall, at least one micro-hole in the sidewall of the needle cannula, and a flexible membrane sealably fixed to an inner surface of the needle cannula. The flexible membrane holds a second medicament between the flexible membrane and a portion of the sidewall having the at least one micro-hole.

The method further includes the step of setting a dose of the primary medicament contained in the primary drug reservoir using a single dose setter of the drug delivery device. The method then includes activating a dose button to cause the set dose of the primary medicament from the primary reservoir to flow in a distal direction. Finally, the method includes forcing the primary medicament to flow through the needle cannula, wherein the hydraulic pressure exerted by the primary medicament forces the second medicament to flow out the at least one micro-hole to a first injection depth. The primary medicament is then able to flow out of the principle (i.e., distal) outlet of the cannula and into a second, axially separated (i.e., deeper) injection depth.

A medicated module in accordance with Applicant's proposed concept can be designed for use with any drug delivery device with an appropriate compatible interface. However, it may be preferable to design the module in such a way as to limit its use to one exclusive primary drug delivery device (or family of devices) through employment of dedicated or coded features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit of Applicant's method and system is that the method and system allow for delivery of medicament to two effectively separate depths within an injection site via a single dispense interface. Delivering medicament to two effectively separate injection depths may be beneficial for a variety of reasons. For example, this may be advantageous for treatments where two medicaments are preferentially taken in combination, but where the ideal target depth for each medicament is different. For instance, drugs that are best delivered into the dermis (e.g., for systemic circulation) can be provided at the same time (i.e., in the same injection) as drugs that are best delivered into the subcutaneous tissue. By way of an example, providing a dose of an analgesic medicament, or an anti-inflammatory medicament to the dermis (a region generally about 2 millimeters (mm) thick that lies approximately 1 mm below the surface of the skin, depending on location) during the injection of a medicament, such as an insulin, into the subcutaneous tissue may be beneficial in reducing pain or inflammation of the area after the treatment has been performed. As another example, this may be advantageous in situations where the dilution of one (or both) of the medicaments with the other could have a significantly adverse affect on the medicaments Pharmacokinetic (PK) profile. It is known in the art that the PK profile of insulins can be effected by the concentration in which the dose is provided (even if the amount of insulin units in the dose is the same in both instances)

In a preferred embodiment, the primary drug delivery device is used more than once and therefore is a multi-use device; however, the drug delivery device may also be a single use disposable device. Such a device may or may not have a replaceable reservoir of the primary drug compound, but our proposed concept is equally applicable to both scenarios. It is also possible to have a suite of different medicated modules for various conditions that could be prescribed as one-off extra medication to patients already using a standard drug delivery device. Should the patient attempt to reuse a previously used medicated module, features may be present that prevent reattachment to a primary drug delivery device or that prevent or discourage subsequent dosing through the needle via alternative means. For example, this module may include a locking needle guard that is activated after a user delivers a dose from the medicated module. Other means of alerting the user may include some (or all) of the following:

Physical prevention of medicated module re-attachment to the primary drug delivery device once the module has been used and removed.

Physical/hydraulic prevention of subsequent liquid flow through the drug dispense interface once it has been used.

Physical locking of the dose setter and/or dose button of the primary drug delivery device.

Visual warnings (e.g., change in color and/or warning text/ indicia within an indication window on the module once insertion and/or fluid flow has occurred).

Tactile feedback (presence or absence of tactile features on the outer surface of the module hub following use).

A further proposed feature is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Applicant's proposed concept is a system and method for dispensing to effectively separate injection depths a non-user settable dose of a secondary medicament and a user-settable dose of a primary medicament using a single dispense interface. Generally, Applicant's proposed medicated module includes a medicated needle cannula that stores or retains a fixed-dose of a secondary medicament. The medicated needle also includes at least one micro-hole in a sidewall of the needle cannula, and the second medicament can be dispensed through the at least one micro-hole. The medicated needle cannula facilitates delivery of medicament to two effectively different injection depths within a single injection 'site'.

Figure 1:
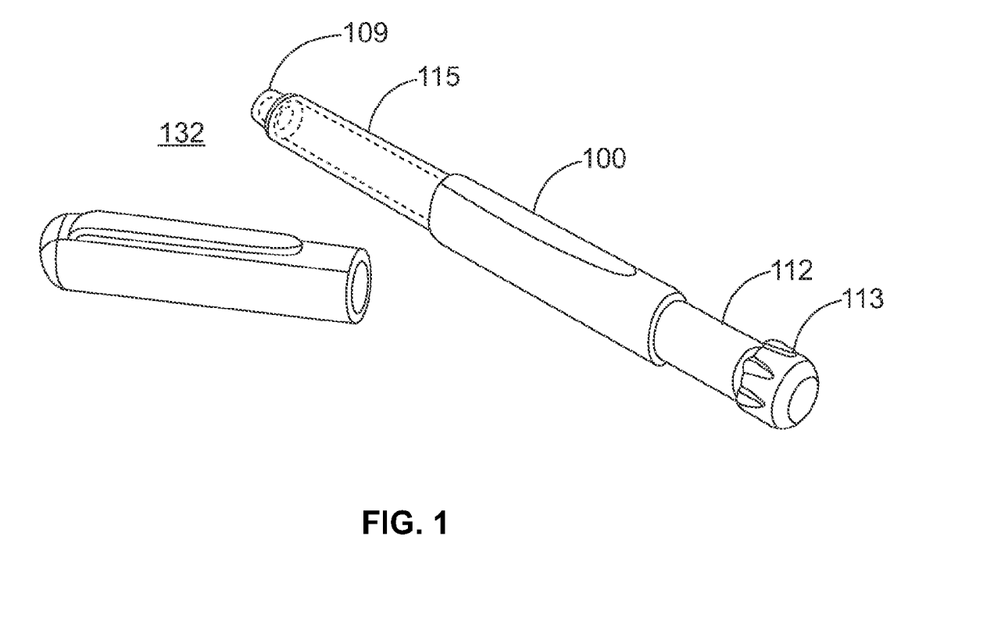
FIG. 1 illustrates a perspective view of one possible drug delivery device that can be used with Applicant's proposed medicated modules.

A medicated module in accordance with embodiments of Applicant's proposed concepts may be attached to a primary drug delivery device, such as drug delivery device 100 shown in FIG. 1. Specifically, the medicated module can be attached to the connection means 109 of distal end 132. A medicated module in accordance with Applicant's proposed concept is preferably self-contained and provided as a sealed and sterile disposable module that has an attachment means compatible to the attachment means 109 at the distal end 132 of device 100. Although not shown, the medicated module could be supplied by a manufacturer contained in a protective and sterile container, where the user would peel or rip open a seal or the container itself to gain access to the sterile medicated module. Further, the drug delivery device 100 includes a housing including a single dose setter 112. The dose setter 112 may be operably connected to a primary reservoir of medicament that may be stored in the drug delivery device, such as in cartridge holder 115. The user may use a dose dial button 113 in order to dial a user selectable dose of the primary medicament.

Applicant's proposed concept is a medicated module that is attachable to a drug delivery device such as drug delivery device 100 that has a drug reservoir holding a first, primary medicament. In a first embodiment of Applicant's proposed concept, the medicated module includes a needle cannula having a sidewall and at least one micro-hole in the sidewall of the needle cannula. The module may also include a flexible membrane sealably fixed to an inner surface of the needle cannula. The flexible membrane holds a second medicament between the flexible membrane and a portion of the sidewall having the at least one micro-hole. During dispense, the primary medicament is forced out of the distal end of the needle cannula and the second medicament is forced out the micro-holes of the needle cannula due to pressure created by the primary medicament.

Figure 2:
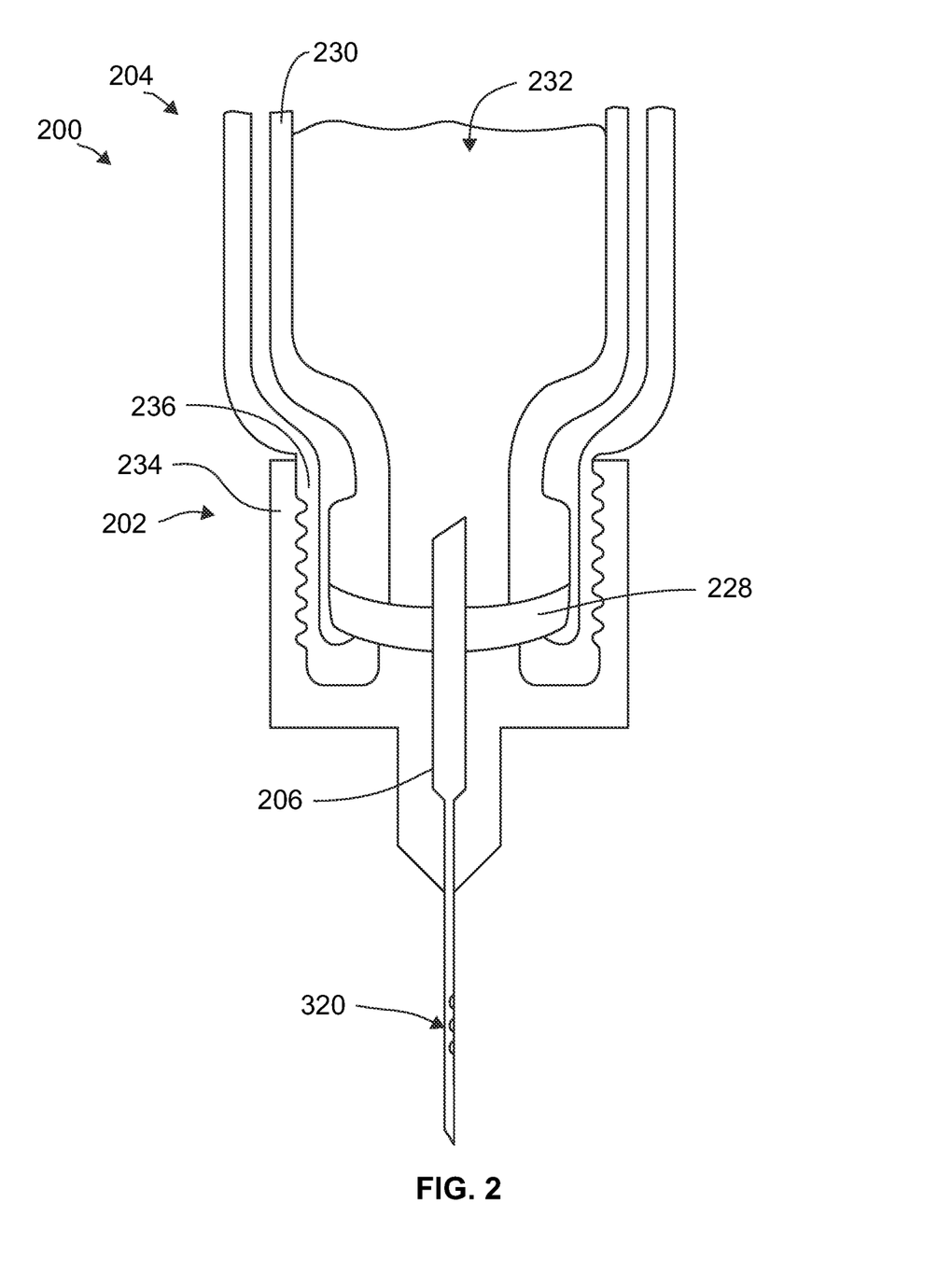
FIG. 2 illustrates a cross-sectional view of an exemplary medicated module attached to an exemplary drug delivery device.

FIG. 2 illustrates a drug delivery system 200 including an exemplary medicated module 202 and primary drug delivery device 204 that contains a first, primary medicament 232. In this Figure, only a partial view of the distal end of the primary drug delivery device 204 is shown. Primary drug delivery device 204 may be the same as or similar to drug delivery device 100 of FIG. 1. The medicated module 202 includes a double-ended medicated needle cannula 206. The needle cannula 206 engages with or communicates with the reservoir 230 of drug delivery device 204 when the module and device are attached to one another. Further, the needle cannula 206 may be used to subcutaneously inject medicament into a user of drug delivery system 200. It should be understood, however, that, in alternative embodiments, the medicated module may comprise two separate needles. Specifically, a first needle cannula may serve as an engagement needle to establish fluid communication with the primary reservoir and a second needle cannula may serve as an output needle to facilitate injection of medicament to a user.

Generally, medicated needle cannula 206 holds a second medicament 320 and is configured such that it can deliver (i) second medicament 320 to one injection depth and (ii) primary medicament 232 to a different injection depth within the same injection site. Medicated needle cannula 206 will be described in greater detail with reference to FIGS. 3a and 3b.

The medicated module 202 also includes an attachment means 234. The attachment means 234 is configured to attach to a corresponding attachment means of a drug delivery device, such as the attachment means 236 of drug delivery device 204 (or, in another example, the attachment means 109 at the distal end 132 of device 100). Further, in an embodiment, the medicated module 202 also includes a needle cover or needle guard (not shown). A needle cover may have a connection feature (e.g., a snap-fit feature) that allows the cover to be removably attached to the body of the medicated module 202. A needle cover or needle guard may substantially conceal the needle cannula 206 from a user's view so as to beneficially reduce any needle anxiety that a patient may be experiencing. While substantially concealing the needle, the needle cover or needle guard also helps to prevent inadvertent needle sticks.

FIG. 2 depicts the medicated module 202 after the module is attached to drug delivery device 204 and prior to injection. Attachment of medicated module 202 to drug delivery device 204 causes the proximal end of the needle cannula 206 to penetrate the septum 228 of the drug cartridge or reservoir 230 of the drug delivery device 204. Once the needle cannula 206 has passed through the septum 228 of the cartridge 230, fluid connection is made with the first, primary medicament 232. In other words, the needle cannula 206 is capable of fluid communication with the drug reservoir 230. After the module 202 is attached to the device 204, a user may set a user-settable dose of the first medicament 232. The dose of the drug delivery device may be set in a usual manner (e.g., by dialing out an appropriate number of units of the primary medicament 232 with a dose dial). Dispense of the first and second medicaments 232, 320 may then be achieved via activation of the dosing mechanism of the drug delivery device. The dispense of the first and second medicament is described below with reference to FIGS. 3a and 3b.

Figure 3A:
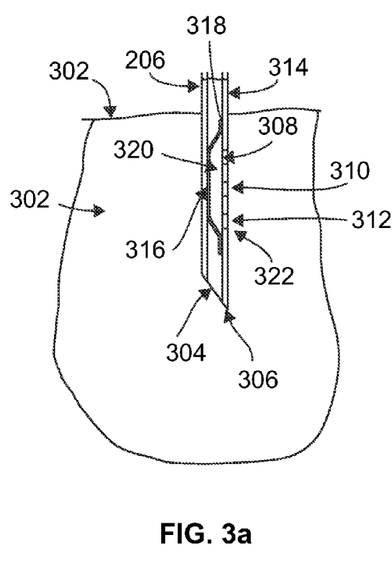
FIG. 3a illustrates a cross-sectional view of an exemplary medicated needle of an exemplary medicated module.
Figure 3B:
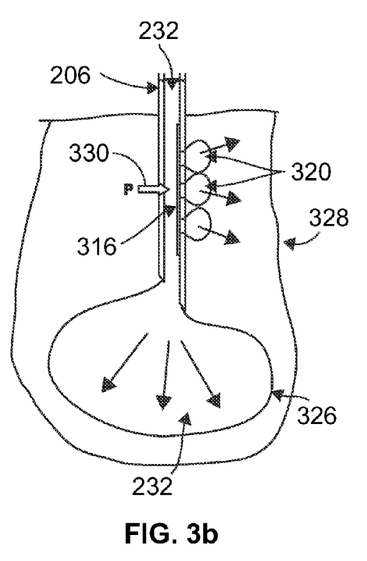
FIG. 3b illustrates a cross-sectional view of the exemplary needle of FIG. 3a during dispense.

FIGS. 3a and 3b illustrate a close-up, cross-sectional view of a distal end of needle cannula 206 of medicated module 202. In these Figures, the medicated needle cannula 206 is depicted as piercing the skin 302 of a user of the drug delivery system 200. The needle cannula 206 comprises an output port 304 at the distal end 306 of the needle. The needle cannula 206 also includes micro-holes 308, 310, and 312 located in the sidewall 314 of the needle. Additional or fewer micro-holes are possible. A flexible membrane 316 is sealably fixed to an inner surface 318 of the needle cannula 206. The flexible membrane 316 holds a secondary medicament 320 between the flexible membrane 316 and a portion 322 of the sidewall having the micro-holes 308, 310, and 312. The second medicament 320 is in direct fluid communication with the micro-holes 308, 310, and 312. However, due to a combination of the surface tension of the medicament 320 and the small diameter of the micro-holes, the medicament 320 is unable to leak out from the micro-holes prior to dispense. Applicant notes that the use of the term "micro" to describe the micro-holes 308, 310, and 312 is not meant to be limiting. The term is used solely to convey the small diameter of the holes; however, the micro-holes 308, 310, 312 may simply be referred to as holes 308, 310, and 312.

In an example, the first medicament 232 comprises insulin and the second medicament 320 comprises GLP-1. However, other medicaments and/or combinations of medicament are possible. Further, the flexible membrane 316 preferably is not permeable, so that the secondary medicament 320 does not mix with the primary medicament 232 during the dispense process. Example materials that the membrane 316 could be manufactured from include, but are not limited to, polyvinylidene chloride (PVdCl), LDPE (low density polyethylene), and LLDPE (linear low density polyethylene). Alternatively the membrane may be constructed from a multi-layer foil, such as, but not limited to, PE (Polyethylene) with a PET (Polyethylene terephthalate) coating for example. Still further, the flexible membrane 316 may be sealed to the inner wall 318 using any suitable means, such as an adhesive or resin.

The micro-holes preferably have a sufficiently small diameter so that the medicament 320 does not leak out prior to dispense. The diameter of the micro-holes required to prevent a medicament from leaking out may depend on the surface tension of the medicament that is contained in the needle cannula. Thus, in various examples of Applicant's medicated needle cannula, the size of the micro-holes may vary. In an example, a diameter of each micro-hole may be between 0.03 and 0.08 millimeters (mm). Micro-holes of this size may prevent medicament having fluid properties (e.g., viscosity, surface tension, etc) similar to those of water (or higher) from leaking out of the micro-holes. It should, however, be understood that these values are merely intended as examples only. Other diameters and fluid properties are possible as well.

A user may begin the dispense process by activating a dose button of primary drug delivery device 204. As shown in FIG. 3b, during the dispense stroke, the primary medicament 232 from drug delivery device 204 is injected out output port 304 of the medicated needle cannula 206 into a primary injection depth 326. The flow of primary medicament 232 applies a hydraulic pressure (P) to one side of the flexible membrane 316, forcing secondary medicament 320 out of the micro-holes 308, 310, and 312 into a secondary injection depth 328. In FIG. 3b, hydraulic pressure "P" is indicated by arrow 330.

In other words, during dispense, the first medicament 232 flows through the cannula 206 toward the port 304 at the distal end 306 of the needle cannula and compresses the flexible membrane 316 against the internal sidewall of the cannula 314. The flexible membrane 316 then forces the second medicament out micro-holes 308, 310, and 312 into the injection depth 328.

Provided that the axial spacing between the output port 304 and the micro-holes is sufficient and/or the volumes of medicament dispensed are sufficiently small, then the injection depths 326 and 328 may be considered to be two separate injection depths. Since they are two distinct injection depths, the opportunity for mixing in vivo is eliminated or minimized.

As shown in the example of FIG. 3b, the axial displacement between output 304 and micro-holes 308, 310, and 312 is sufficient so that the dispensed medicament delivered to the injections depths 326 and 328 has minimal opportunity to interact with one another (e.g., mix) in vivo. As mentioned previously, delivering medicament to two different injection depths may be beneficial where two medicaments are preferentially taken in combination, but where the ideal target depth for each is different, or in situations where the dilution of one (or both) of the medicaments with the other could have an adverse effect on its PK profile.

The different depths of injection, in an example, could correspond to different layers of the user's skin. For instance, second medicament 320 may be delivered to the dermis layer, while first medicament 232 may be delivered to a deeper layer, such as the subcutaneous layer. Other examples are possible as well. The axial displacement between the output hole and the micro-holes may vary, and the displacement may depend on the desired dispense outcome. In an example, the micro-holes may be located between 5.5 and 7 mm above the output port 304.

Figure 5:
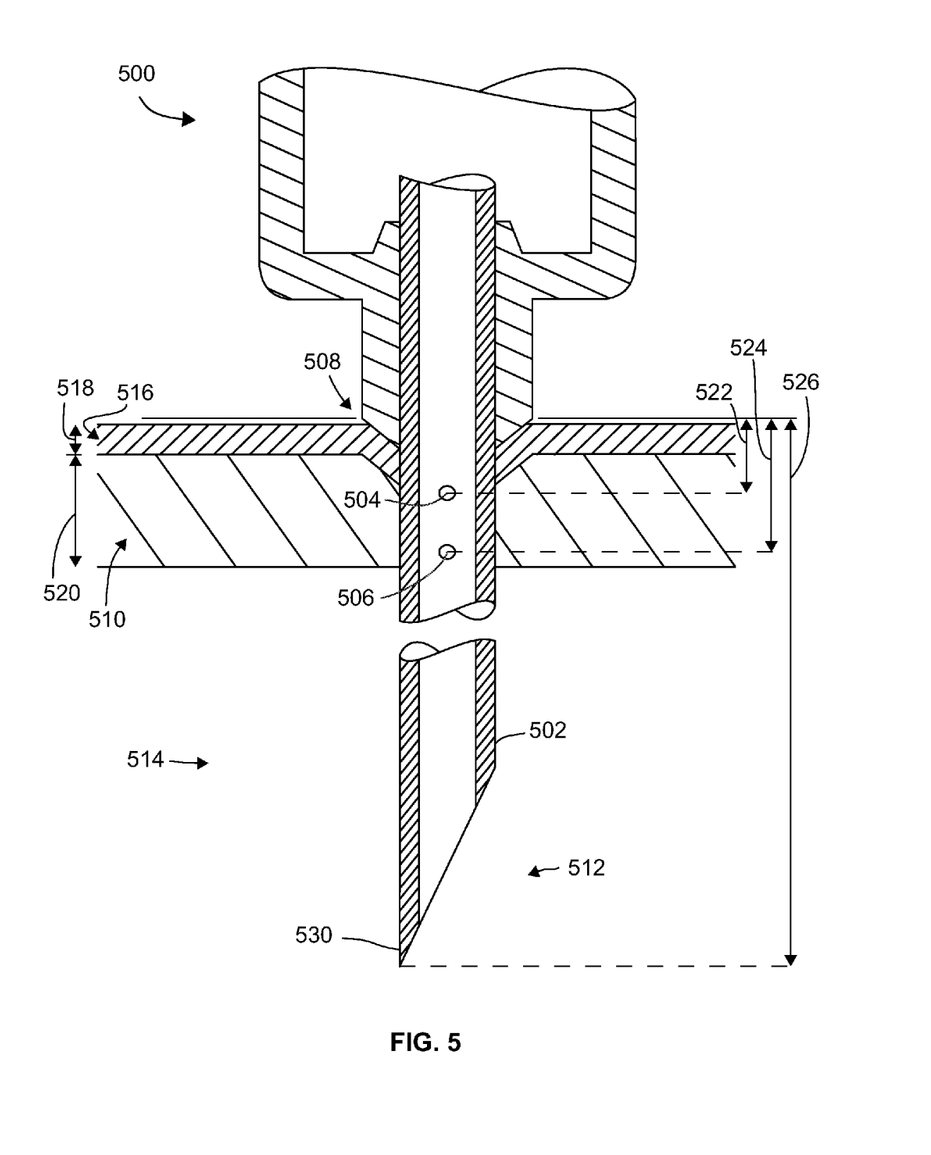
FIG. 5 illustrates a cross-section view of an exemplary medicated module that is configured to deliver a primary dose to a subcutaneous layer of a user and a secondary dose to a dermis layer of the user.

A particular example of different injection depths is shown in FIG. 5. Medicated module 500 includes a needle cannula 502 that includes side holes 504 and 506. When the needle cannula 502 is fully inserted into an injection site 508 of a user, the side holes 504 and 506 reach a depth that is located in the dermis layer 510 of the user' skin, and the distal end or output port 512 of the cannula 502 reaches a second depth that is located in the subcutaneous layer 514. In this example, in order for the side holes 504, 506 to be located in the dermis layer 510 when the cannula 502 is fully inserted in injection site 508, the first side hole 504 is located at a depth 522 below the injection site, and the second side hole 506 is located at a depth 524 below the injection site. The distal end 530 of the cannula is located at a depth 526 below the injection site.

As mentioned above, depths 522 and 524 are located in the dermis layer 510 and depth 526 is located in the subcutaneous layer 514. In a particular example, the epidermis layer 516 may be located directly under the injection site and have a height 518 that is approximately 0.5-1 mm. Further, the dermis layer may have a height 520 that is approximately 2 mm. Therefore, in order to ensure that the side holes 504 and 506 are located in the dermis layer 510 when the cannula is fully inserted (i.e., when the needle hub contacts the injection site 508 and no further penetration is possible), side hole 502 may have a depth 522 of approximately 1.2 mm and side hole 506 may have a depth 524 of approximately 2.4 mm. Further, the distal end 530 may reach a depth 526 of approximately 4 to 12 (or more) mm. It should be understood, however, that these values are intended as examples only, and other values are possible.

In another example of Applicant's proposed concept, the medicated needle cannula may be configured to allow delivery to more than two injection depths (e.g., three different injection depths). This may be accomplished by having two (or more) sets of micro-holes and flexible bladders that are located at different axial heights in the needle cannula.

After completion of the dispense operation, the medicated module 202 may be removed from drug delivery device 204 and disposed of by the patient. This removal may allow subsequent medicated needles to be attached to the primary injection device 204 as and when required.

In some situations, it may be desirable for a user to be able to prime the medicated module 202. For example, the user may want to prime the medicated module 202 to ensure that the primary drug delivery device 204 is functioning properly. As another example, the user may want to prime the medicated module 202 to ensure that the proximal end of the cannula 206 (i.e., the end that pierces the septum 228) is not blocked. Other examples are possible as well. Beneficially, the medicated module 202 may be configured such that, prior to dispense, the medicated module 202 can be primed without forcing the second medicament 320 out micro-holes 308, 310, and 312.

Different elements of the medicated module may be adjusted to allow the module to be primed. In particular, the following elements of the design may be considered: (i) the size of the micro-holes in the sidewall of the cannula; (ii) the size and/or elastic modulus of the flexible membrane within the cannula bore; and (iii) the viscosity and/or surface tension characteristics of the second medicament 320 within the flexible bladder. Manipulation of these elements may allow the system to be adjusted such that the pressure differential required to force the second medicament 320 out through the micro-holes 308, 310, and 312 is greater than the pressure generated in the primary medicament 232 during priming (where the dose is dispensed slowly to atmosphere and hence relatively low) but is less than the pressure generated in the fluid during injection into subcutaneous tissue (which, due to back pressure created by the fluidic resistance of the human body, is higher). Therefore, during priming, the first medicament 232 may flow through cannula 206, pass the flexible membrane 316, and flow out output 304, without causing the second medicament to be dispensed from the micro-holes.

Figure 4A:
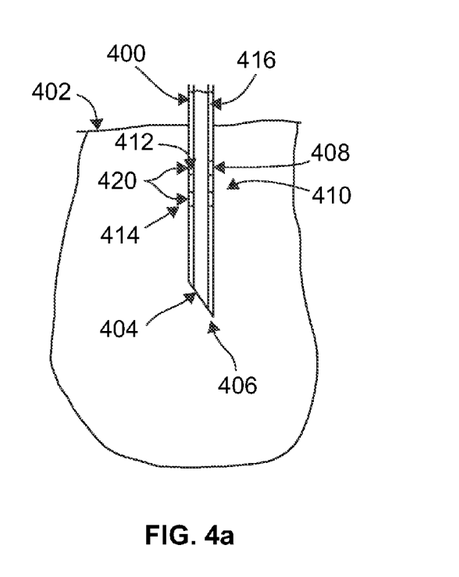
FIG. 4a illustrates a cross-sectional view of an exemplary medicated needle of an exemplary medicated module.
Figure 4B:
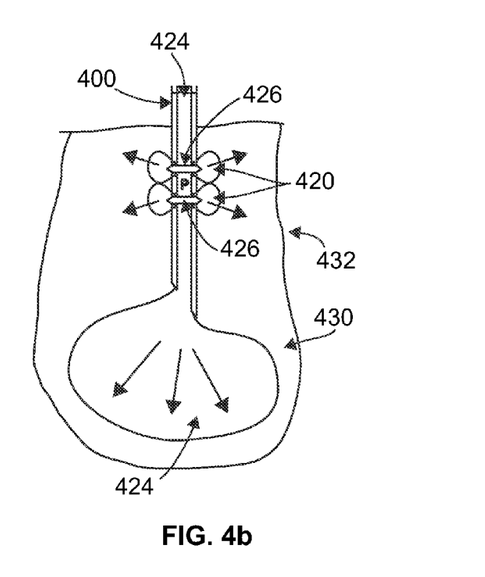
FIG. 4b illustrates a cross-sectional view of the exemplary medicated needle of FIG. 4a during dispense.

In some treatment situations, mixing of two different medicaments or combinations of medicaments in vivo is acceptable and/or desirable, but delivery to different injection depths is still preferred. For example, it may be preferable to deliver doses of medicament to two different delivery depths as explained earlier above. FIGS. 4a and 4b depict a medicated needle cannula 400 that may be used in instances where it is acceptable for an amount of mixing between two medicaments to occur in vivo, but delivery to two injection depths is still preferred. The medicated needle cannula 400 may be disposed in a medicated module, such as the medicated module depicted in FIG. 2.

FIGS. 4a and 4b illustrate a close-up, cross-sectional view of a distal end of the medicated needle cannula 400. In these Figures, the medicated needle cannula 400 is depicted as piercing the skin 402 of a user of the medicated needle cannula. The needle cannula 400 comprises an output port 404 at the distal end 406 of the needle cannula 400. The needle cannula 400 also includes micro-holes 408, 410, 412, and 414, each located in the sidewall 416 of the needle cannula. The micro-holes 408, 410, 412, and 414 hold a secondary medicament 420.

During dispense, the secondary medicament 420 is in direct fluid communication with the micro-holes 408, 410, 412, and 414, and the dose of secondary medicament 420 may be held in the micro-holes 408, 410, 412, and 414 in various ways. How the dose of medicament is held in the micro-holes may depend on the form that the secondary medicament 420 takes. For example, for liquid-based formulations, the dose of medicament may be held in place due to surface tension/viscosity effects. Alternatively, the dose could be in the form of a compressed powder. Further, similar to the embodiment discussed above with respect to FIG. 3, the micro-holes preferably have a sufficiently small diameter so that the medicament 420 does not leak or fall out. Once again, it should be understood that the size required to prevent a medicament from leaking out may depend on the fluid properties of the medicament that is contained in the needle cannula. Thus, in various examples of this embodiment, the size of the micro-holes may vary. In an example, a diameter of each micro-hole is between 0.03 and 0.08 mm. Micro-holes of this size may prevent medicament having fluidic properties similar (or greater) than that of water from leaking out of the micro-holes. As another example, for powder-based formulations, the dose of medicament 420 may be held in place due to, for example, conglomeration, compaction, unconfined yield strength, and/or sheer strength effects.

A medicated module including medicated needle cannula 400 may be attached to a drug delivery device holding a primary medicament, such as primary medicament 424. The dose of the drug delivery device may be set in a usual manner (e.g., by dialing out an appropriate number of units of the primary medicament 424 with a dose dial). Dispense of the first and second medicaments 424, 420 may then be achieved via activation of the dosing mechanism of the drug delivery device. A snapshot of dispense from the medicated needle cannula 400 is shown in FIG. 4b.

During dispense, the primary medicament 424 forces the secondary medicament 420 through micro-holes 408, 410, 412, and 414. In particular, the back pressure created in the needle cannula 400 by virtue of the fluidic resistance of human tissue can cause a small amount of the first medicament 424 to be forced out of the micro-holes 408, 410, 412, and 414, entraining the second medicament 420 with it (either as two liquids separated by a boundary layer, or as a reconstituted mix). As shown by arrows 426, pressure "P" forces the secondary medicament 420 out from the micro-holes. During injection, the primary medicament 424 will be delivered out output 404 to first injection depth 430, and the secondary medicament 420 (along with a small amount of primary medicament 424) will be delivered out the various micro-holes to second injection depth 432.

Provided that the axial spacing between the output 404 and the micro-holes is sufficient and/or the volumes of medicament dispensed are sufficiently small, then the injection depths 430 and 432 may be considered to be two separate injection depths. Thus, the medicated needle cannula 400 is beneficially operable to deliver medicament to two different injection depths. For instance, injection depth 432 could be located in the dermis layer, and injection depth 430 could be located in the subcutaneous layer.

Similar to the example described with respect to FIGS. 2-3, in some examples of this second embodiment, the medicated needle cannula 400 may be primed with the primary medicament from the primary drug delivery device the medicated needle cannula is attached to. If the secondary medicament is a liquid, through manipulation of its fluidic properties (principally surface tension and viscosity) of the second medicament and the size of the micro-holes, this alternative embodiment could permit priming of the first medicament 424. Therefore, during priming, the first medicament does not force the second medicament from the at least one micro-hole. If the secondary medicament is a powder, priming may be possible. However, in some circumstances, the powder may become saturated with fluid and may either be expelled via the side holes or may be entrained in the primary dose, and in such a circumstance a priming operation may preferably not be performed.

Additionally, in some examples of this second embodiment, the medicated needle cannula may be configured to allow delivery to more than two injection depths (e.g., three different injection depths). This may be accomplished by having two (or more) sets of micro-holes that are located at different axial heights.

Applicant's proposed concept also includes a method for delivering a primary medicament to a first injection depth and a second medicament to a second injection depth using a single dispense interface. The method includes the step of attaching a medicated module to a drug delivery device, such as the medicated module and drug delivery device illustrated in FIG. 2. As described above, the drug delivery device has a primary drug reservoir holding the primary medicament. Further, the medicated module may include a needle cannula having a sidewall, at least one micro-hole in the sidewall of the needle cannula, and a flexible membrane sealably fixed to an inner surface of the needle cannula. The flexible membrane may hold a second medicament between the flexible membrane and a portion of the sidewall having the at least one micro-hole. The method further includes the step of setting a dose of the primary medicament contained in the primary drug reservoir using a single dose setter of the drug delivery device. The method then includes activating a dose button to cause the set dose of the primary medicament from the primary reservoir to flow in a distal direction. Finally, the method includes forcing the primary medicament to flow through the needle cannula, wherein the primary medicament forces the second medicament to flow out the at least one micro-hole. A similar method using a medicated module that includes a medicated needle cannula such as medicated needle cannula 400 is also possible.

As described above, Applicant's proposed concept beneficially allows for delivering doses of medicament to two separate injection depths within the same injection site using a single drug delivery system having a single dispense interface. Specifically, in the first embodiment, Applicant's proposed concept beneficially allows for delivery of a first medicament to a first injection depth and a second medicament to a second injection depth. Due to the delivery of the medicaments to separate injection depths, the two medicaments have limited or no opportunity for mixing in vivo. Further, in the second embodiment, where some mixing of a primary medicament and secondary medicament is acceptable and/or desirable, Applicant's proposed concept allows for delivery of the medicament using a single dispense interface to two different injection depths.

The connection or attachment between the medicated module of the above described embodiments may contain additional features (not shown), such as connectors, stops, splines, ribs, grooves, and the like design features, that ensure that specific medicated module are attachable only to matching drug delivery devices. Such additional features would prevent the insertion of a non-appropriate medicated module to a non-matching injection device.

The medicated module can be manufactured from plastic, glass, or other drug contact suitable material. The integrated medicated output needle cannula can be any needle cannula suitable for subcutaneous or intramuscular injection. Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user.

The medicated module of Applicant's concept should be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical drug delivery device contains a cartridge or other reservoir of medication. This cartridge is typically cylindrical in shape and is usually manufactured in glass. The cartridge is sealed at one end with a rubber bung and at the other end by a rubber septum. The drug delivery pen is designed to deliver multiple injections. The delivery mechanism is typically powered by a manual action of the user, however, the injection mechanism may also be powered by other means such as a spring, compressed gas or electrical energy.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module attachable to a drug delivery device, the drug delivery device having a drug reservoir holding a first medicament, the medicated module (202, 500) comprising:
   a needle cannula having a sidewall;
   at least one micro-hole in the sidewall of the needle cannula;
   a flexible membrane sealably fixed to an inner surface of the needle cannula, wherein the flexible membrane holds a second medicament between the flexible membrane and a portion of the sidewall having the at least one micro-hole.

2. The medicated module of claim 1, wherein the second medicament is in direct fluid communication with the at least one micro-hole.

3. The medicated module of claim 2, wherein each micro-hole has a diameter of the at least one micro-hole is between 0.03 and 0.08 millimeters (mm).

4. The medicated module of claim 1, wherein, after attachment to the drug delivery device, the needle cannula is in fluid communication with the drug reservoir,
   wherein, during dispense, the first medicament flows through the needle cannula toward an output at a distal end of the needle cannula and compresses the flexible membrane against the sidewall, and
   wherein the flexible membrane forces the second medicament out the at least one micro-hole.

5. The medicated module of claim 4, wherein, prior to dispense, the medicated module can be primed with the first medicament without forcing the second medicament out of the at least one micro-hole.

6. The medicated module of claim 5, wherein a pressure differential required to force the second medicament out of the at least one micro-hole is greater than a pressure generated by the first medicament during priming.

7. The medicated module of claim 4, wherein at least one of the at least one micro-hole is located at about 1.2 millimeters (mm) below the injection site.

8. The medicated module of claim 7, wherein each micro-hole of the at least one micro-hole is located between 5.5 to 7 mm above the output.

9. The medicated module of claim 4, wherein the first medicament is delivered to a first injection depth, and wherein the second medicament is delivered to a second injection depth different from the first injection depth.

10. The medicated module of claim 9, wherein the first injection depth corresponds to a subcutaneous layer of a user's skin, and wherein the second injection depth corresponds to a dermis layer of the user.

11. A needle cannula comprising:
    a sidewall;
    at least one micro-hole in the sidewall of the needle cannula;
    a flexible membrane sealably fixed to an inner surface of the needle cannula, wherein the flexible membrane holds a medicament between the flexible membrane and a portion of the sidewall having the at least one micro-hole.

* * * * *